United States Patent [19]

Moutafis et al.

[11] Patent Number: 4,968,300
[45] Date of Patent: Nov. 6, 1990

[54] BALLOON STRETCH MECHANISM

[75] Inventors: Timothy E. Moutafis, Gloucester; Fredric L. Milder, Brookline, both of Mass.

[73] Assignee: Abiomed Limited Partnership, Danvers, Mass.

[21] Appl. No.: 253,678

[22] Filed: Oct. 5, 1988

[51] Int. Cl.⁵ ............................................. A61M 25/10
[52] U.S. Cl. ...................................... 604/96; 606/194
[58] Field of Search ............................ 604/96–103, 604/197, 198, 104–107, 210, 208; 600/18; 128/344, 348.1; 606/192, 194

[56] References Cited

U.S. PATENT DOCUMENTS

| | | | |
|---|---|---|---|
| 2,556,783 | 5/1950 | Wallace | 604/105 |
| 3,380,448 | 4/1968 | Sadove et al. | 604/263 |
| 3,799,172 | 3/1974 | Szpur | 604/105 |
| 4,077,394 | 3/1978 | McCurdy | 600/18 |
| 4,276,875 | 7/1981 | Wolvek | 604/96 |
| 4,315,512 | 2/1982 | Fogarty | 128/344 |
| 4,403,612 | 9/1983 | Fogarty | 128/348.1 |
| 4,552,127 | 11/1985 | Schiff | 600/18 |
| 4,644,936 | 2/1987 | Schiff | 128/344 |

Primary Examiner—Michael H. Thaler
Assistant Examiner—William Lewis
Attorney, Agent, or Firm—Lahive & Cockfield

[57] ABSTRACT

A mechanism advances to stretch an intraaortic balloon prior to insertion or removal. One embodiment includes a member which extends through a catheter from the handle to the balloon, and which advances to extend the balloon without appreciably twisting it. A spring detent assembly in the handle defines a precise amount of extension delivered by the member. The mechanism permits the balloon to be fully relaxed once it is inserted and to be recompacted, following use, for removal from the patient. The device is of particular utility for a large diameter, irregular or polygonal non-cylindrical balloon, and for inserting a balloon along an arterial path having a narrow passage or sharp curve.

11 Claims, 7 Drawing Sheets

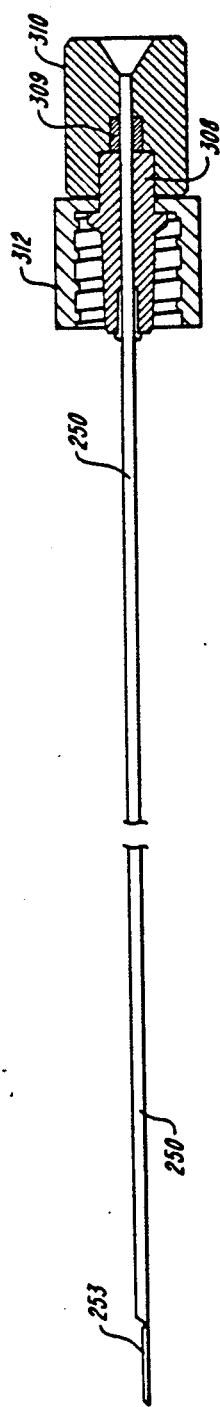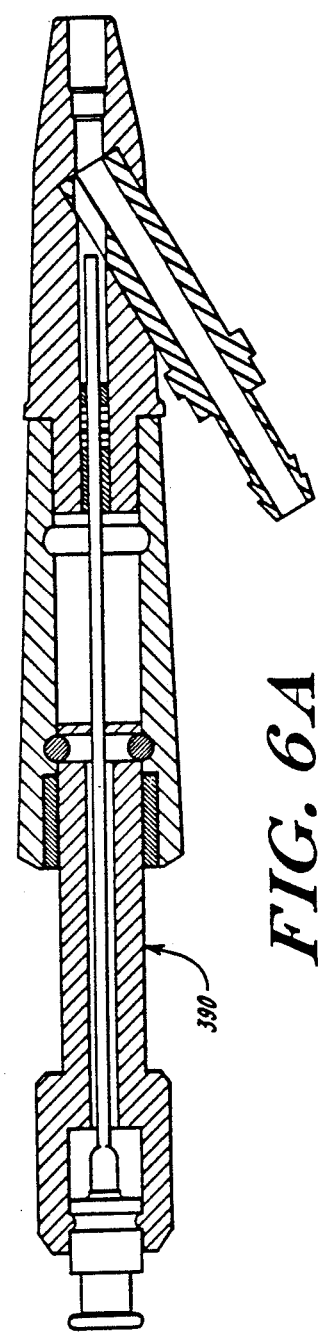
FIG. 5
FIG. 6A

BALLOON STRETCH MECHANISM

BACKGROUND OF THE INVENTION

The present invention relates to the field of intraaortic balloon pumps, and more particularly to methods and apparatus for the insertion of such balloon pumps.

A conventional intraaortic balloon pump (IABP) consists essentially of a balloon or bladder which is mounted at the tip of an inflation tube. The balloon may have dimensions of approximately one and one-half centimeters diameter by twenty-two centimeters length, and is initially uninflated. In order to insert the balloon, it is folded or otherwise compacted so that its maximum diameter is approximately that of the inflation tube, or about three to six millimeters.

In a basic variation of the conventional Seldinger technique, such an IABP is inserted via a minor artery by first using a guide wire and dilator to establish a path to the desired location in the aorta, and extending a sheath and dilator along the guide wire to its end. The dilator is removed, leaving the sheath in place. Finally, the folded or wrapped balloon is inserted by pushing its inflation tube through the sheath, thus positioning the balloon at the desired spot. This insertion procedure requires that the balloon occupy a relatively small space.

A number of constructions have been proposed in which a balloon is compacted by inserting a special wrapping wire through the catheter to engage the tip of the balloon, and the wire is turned to turn the balloon tip with respect to the catheter. This twists the balloon around the wrapping wire or a central balloon supporting member. Constructions of a more tangential nature are also known in the field of balloon catheterization, wherein a highly extensible balloon is inflated within an artery to widen the arterial passage. Unlike the balloon of an IABP, the balloons used for this purpose generally have a relaxed or uninflated state which is already highly compact, so that insertion mechanisms are not clearly analogous. Examples of some of the foregoing constructions are shown in U.S. Pat. Nos. 4,362,150 of Lombardi, et al.; 4,531,512 of Wolvek et al.; 4,311,133 of Robinson and 4,292,974 of Fogerty. Other constructions provide a rotatable support member about which the balloon is rolled or twisted, possible with the aid of an external balloon-restraining or engaging member.

OBJECTS AND SUMMARY OF THE INVENTION

It is an object of the invention to provide a method and apparatus for facilitating insertion of an intraaortic balloon.

It is another object of the invention to provide a method and apparatus for insertion of a balloon having a shape which is relatively large or irregular compared to the arterial passage.

It is another object of the invention to provide a method and apparatus for insertion of a balloon along a bent or tortuous path.

These and other desirable ends are attained by providing a mechanism for extending a balloon to a stretched state prior to insertion. The mechanism includes an extender member which extends through a catheter from the handle to the balloon, and which advances to extend the balloon significantly while twisting it at most a relatively small amount. An actuation assembly is comprised of one part, preferably a grooved sleeve, in the handle, and a cooperating part, preferably a shank, affixed to the extending member and having a mating protrusion sliding in the groove. This defines a precisely aligned and controlled balloon extension for compacting the balloon when the extender member is advanced. The mechanism permits the balloon to be fully relaxed once it is inserted, and to be recompacted, following use, for removal from the patient.

The device is of particular utility for a large diameter balloon, or for a balloon having a side wall which deviates substantially from straightness, for example, one having a polygonal or highly curved contour. It is of particular utility for inserting a balloon along an arterial path having a narrow passage or a sharp curve.

BRIEF DESCRIPTION OF DRAWINGS

These and other features of the invention will be understood with reference to the description herein of presently preferred embodiments, taken together with the drawings, wherein:

FIG. 5 is a perspective view of an extension member used in the embodiment of FIGS. 3, 4;

FIGS. 6A, 6B show views of another embodiment of a stretch mechanism according to the invention.

DETAILED DESCRIPTION OF ILLUSTRATED EMBODIMENTS

Figure 1:
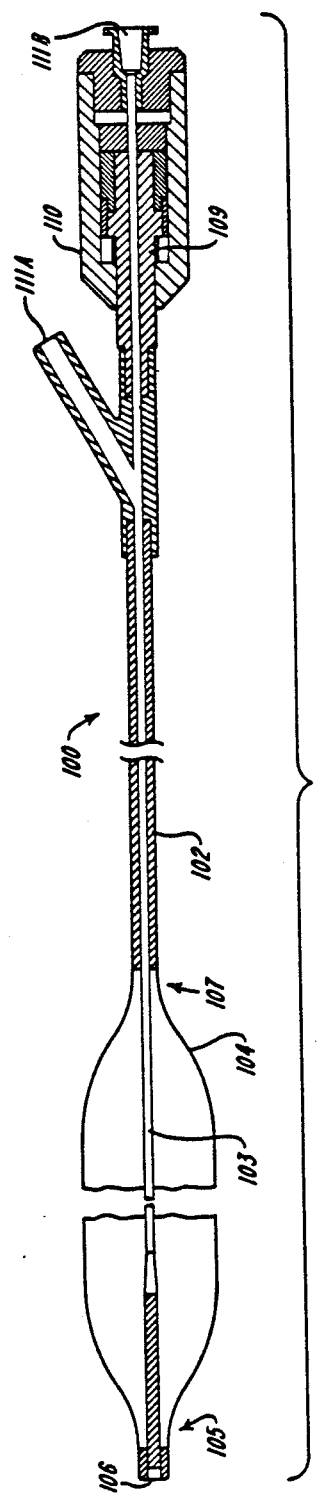
FIG. 1 shows a prior art balloon catheter.

The invention is best understood in relation to the existing art of balloon catheters, of which FIG. 1 illustrates an example 100. Such a device consists of a bladder or balloon 104 formed of a thin walled polymer and having a defined shape, which is integrally connected to an inflation tube 102. Balloon 104 is closed at its distal end 105 and communicates via its other end 107 with the tube 102 so that by applying fluid pressure to the lumen of tube 102, the balloon may be inflated.

An inner tube or support member 103 extends through the balloon to its distal end 105. The near end of tube 102 is connected to a handle 110 which serves as a manifold with ports 111A, 111B for the provision of fluid to, or the sensing of fluid pressures through, the catheter, respectively. In the latter, case, inner member 103 may provide a lumen extending from port 111B to a sensing port 106 at the distal side of the balloon for monitoring fluids at the heart. In the prior art device of FIG. 1, which is taken substantially from a description in U.S. Pat. No. 4,362,150, a threaded member 109 in handle 110 moves the inner member with a rotational motion to effect a large number of turns of the balloon with negligible axial motion in order to compact the balloon 104. The ends 105, 107 are rotationally decoupled, so that the rotational motion of the inner member has the effect of tightly twisting the balloon.

Figure 2A:
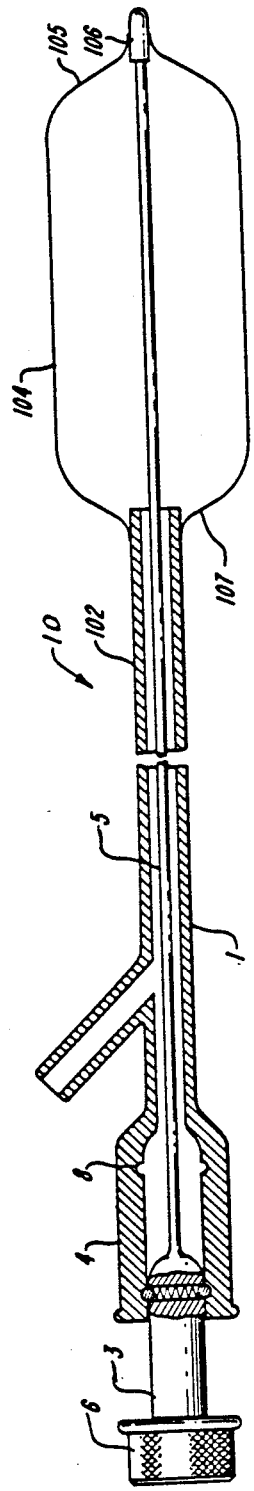
FIGS. 2A, 2B show cross-sectional views of a basic embodiment of a balloon catheter and insertion mechanism according to the invention.
Figure 2B:
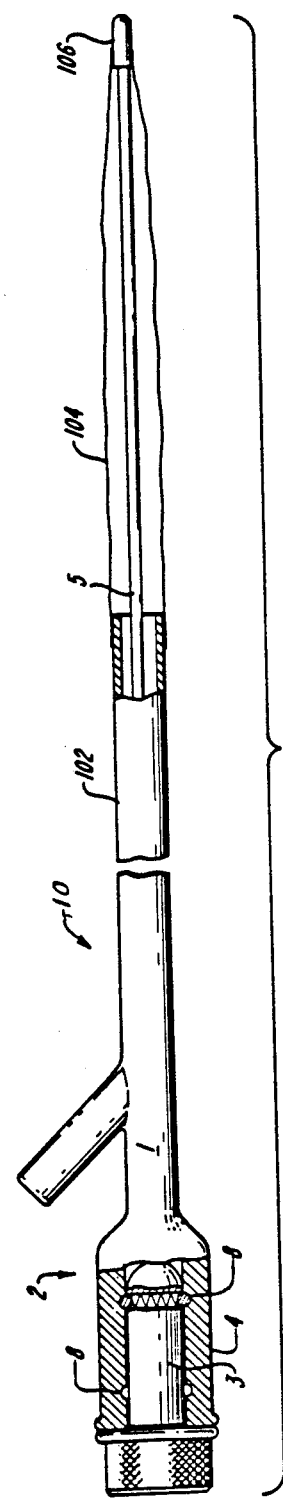

FIGS. 2A, 2B show partial cutaway views of a basic embodiment of a balloon insertion device 10 according to the present invention. For clarity, the view corresponds to that of FIG. 1, and both the balloon and the inflating tube are identified by numerals identical to those used in FIG. 1. In this basic embodiment, a handle portion 1 attached to the tube 102 contains an actuator mechanism 2 which includes an outer aligning sleeve 4 and an inner extender portion 3 which cooperate to move an extender member 5 which runs from the inner portion to the balloon. In this embodiment of the invention, the sleeve and inner member hold the extender in alignment to provide a purely linear displacement in the range of two to five centimeters; a plurality of notched detent positions 8, of which two are illustrated, provide defined stops at known extensions.

Extender member 5 extends the length of the inflation tube 102, which may be, for example, 1.25 meters, and engages a thrust hub 106 of the distal end 105 of the balloon 104. When balloon end 105 is engaged and pushed by the extender member 5, distal end 105 is pushed away from the proximal end 107 of the balloon, and the body of the balloon is stretched and drawn into a compact state. A knurled knob 6 is attached to the end of inner extender portion 3 and permits the user to grip that portion for operation. The two figures, 2A, 2B illustrate the same device in two different extensions.

As shown in FIG. 2A, the actuation mechanism is in its retracted position, so that extender member 5 does not exert force against the balloon, and balloon 104 is in its flaccid, or resting state. In this state, it occupies a relatively large volume, and has a substantially greater diameter than that of the inflation tube 102. As shown in FIG. 2B, the actuation mechanism is fully advanced, and the balloon has been compacted. More precisely, the balloon is stretched by an amount which may be fifteen to seventy-five percent of its resting length, to attain a diameter comparable to that of the inflation tube.

By way of scale, a prototype balloon was made approximately thirty millimeters in diameter and seven centimeters in length. The balloon was non-cylindrical in shape and was also formed with a front-to-back asymmetry. The relatively wide and asymmetrical shape made it difficult to compact the balloon sufficiently for insertion using conventional folding or rolling techniques. Using an actuator mechanism as just described having approximately a 25 millimeter total extension, the balloon was compacted by longitudinal stretching to attain a diameter roughly equal to that of the inflation tube. In this compacted state the balloon was readily inserted through an arterial passage of small diameter.

Figure 3:
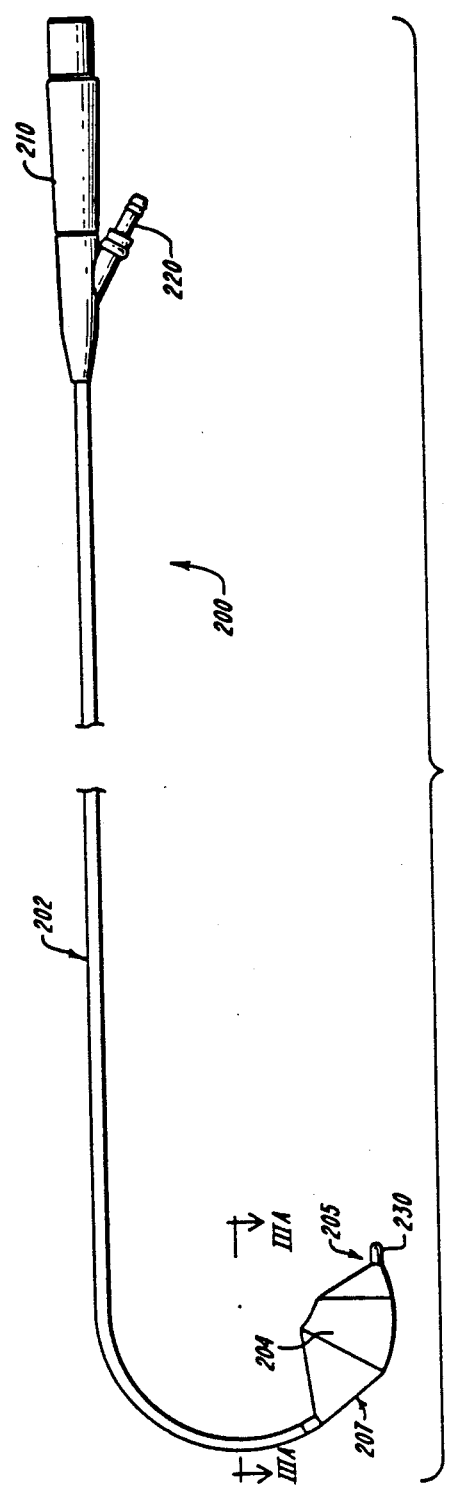
FIGS. 3 and 3A, 3B, and 3C show a schematic view and detailed sectional views of another embodiment of the invention, and variations in balloon tip construction.

FIG. 3 is a schematic representation of another embodiment 200 of the invention, which will be discussed in greater detail below. A balloon 204 is mounted at the end of an inflation tube 202 which extends from a handle 210. The handle constitutes a bifurcation assembly which provides an inflation port 220 interconnected with the balloon 204 via the tube 202, and, as described in greater detail below, an access port for a second tube which communicates with a nosepiece 230 at the distal end of the balloon. The nosepiece, which extends ahead of the balloon, is formed of a strong material, such as polycarbonate. It constitutes a thrust-receiving hub attached to the balloon, like hub 106 of the preceding embodiment, with additional structure for forming a fluid sampling port ahead of the balloon.

Figure 3A:
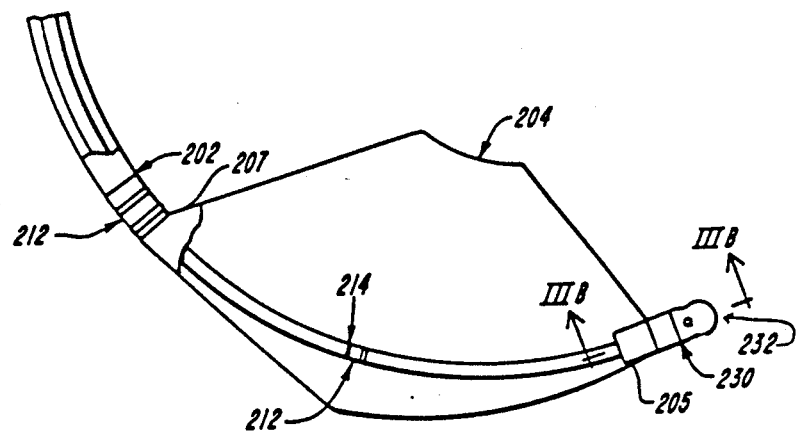

FIG. 3A is a cutaway view of the balloon of FIG. 3, illustrating in further detail internal elements of the balloon and of the set 200. It will be seen that inflation tube 202 seals to the proximal end 207 of the balloon, and that a second or internal tube 214 extends through the inflation tube and connects to the nosepiece 230, which in turn defines an opening or port 232 ahead of the distal end of the balloon. Tantalum markers 212 on each tube 202, 214 permit precise fluoroscopic visualization of the tube end during insertion. Both tubes are made of an appropriate tubing suitable for medical use, such as a polyurethane tube.

Figure 3B:
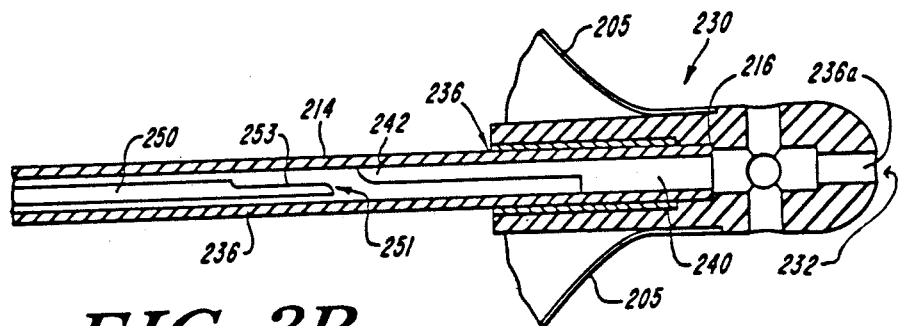

FIG. 3B shows one embodiment of the nosepiece 230 in greater detail, connected to the end 205 of the balloon, forming a central hub with one or more holes communicating with a central passageway 236a to provide a fluid access port for the inner lumen of the device. Nosepiece 230 constitutes a rigid structural member for bearing against a separate extender member which is provided in this embodiment to compact the balloon. Within the nosepiece, inner tube 214 butts against an end wall 216 and is permanently cemented thereto. Within the tube 214, a thrust insert 240 also abuts wall 216 and is press-fit to provide rigid engagement with tube 214 and nosepiece 230. This provides an end assembly against which the extender member may be advanced to extend the balloon forwardly.

The illustrated thrust insert 240 includes a segment of stainless steel tubing having an outer tube diameter matched to the inner diameter of tube 214. At the proximal end of insert 240, approximately one-half the diameter of the insert tube material has been removed and the end beveled, forming an engaging finger 242 in the form a partial tubular shell. The engaging finger 242 is adapted to engage a similarly-shaped solid or hollow end of a metal extender member 250 which is inserted through the tube 214 from handle 210, and which is advanced to stretch the balloon as previously described.

The extender member 250 corresponding to member 5 of FIGS. 2A, 2B is inserted through the inner lumen 236 starting at the handle and extending to the balloon. For clarity of illustration, the distal end 251 of the extender member is shown in FIG. 3B in a position axially withdrawn from the thrust insert 240. One edge of end 251 is flattened, to form finger 253 which engages the similar finger 242 of the thrust insert. The fingers provide an irrotational coupling between member 250 and the balloon tip, eliminating spurious twisting of the balloon. This allows the assembly to maintain precise rotational alignment of the balloon while axially extending it.

Member 250 may be formed of solid or of tubular stock; tubular stock advantageously permits the member to be advanced over a guide wire. Member 250 is preferably removed following balloon insertion for aortic fluid monitoring via the inner lumen. The metal stock used for forming the member 250 and the thrust insert, and the amount of material removed to form the respective (optional) engaging fingers, are selected so that the tube 214 holds the two end regions 242, 253 in firmly engaged alignment. For example, with tube 214 formed of 0.050 ID tubing, a thrust insert 240 was formed of 18 gauge thin wall steel tubing with a flat formed to a depth of 0.021"±0.001" from its nominal 0.050" diameter. This left a 0.029"±0.001" thick protruding finger, or slightly over a semi-diameter of the tubular segment. The corresponding finger of the member 250 was formed of a half-diameter segment of 19 gauge regular wall steel tubing (i.e., 0.027 ID×0.0425 OD) so that the 0.029" thick finger 242 of the thrust insert and the 0.021" thick finger 253 of the extender member 250 are pressed into firm engagement with each other.

The tubing 214 may itself be sufficiently stiff to both push and turn the balloon 204 when its proximal end is moved. Preferably, however, the tubing 214 is pliable and constitutes a relatively ineffective mans for transmission of axial or torsional forces. The provision of the separate internal extender member 250 adds further stiffness which allows the use of appreciably softer tubing materials while providing for the delivery of small but precisely controlled motions to compact the balloon, substantially unperturbed by shear or compression along the length of the inner structure.

It will be appreciated that when firmer catheter or inner tubes are employed, the provision of an irrotational extending member is of less concern, and in that event the fork-like engaging fingers 242, 253 are not necessary. In that case, nosepiece 230 may be formed as a simple hub with a flat or concave thrust-receiving inner face.

Figure 3C:
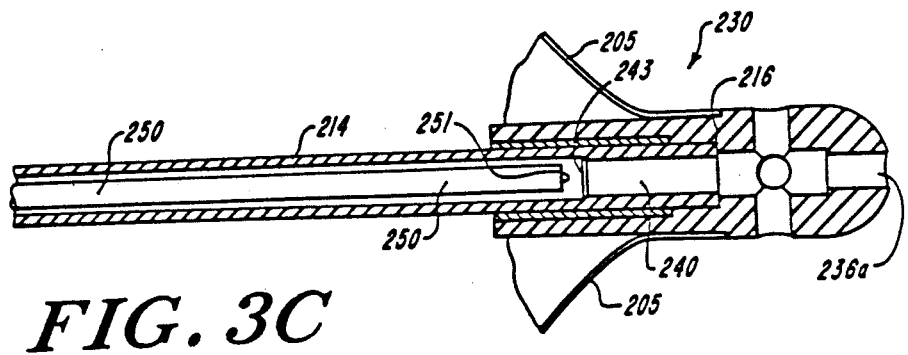

FIG. 3C shows details of the hub and thrust insert of such an embodiment. As shown, extender member 250 has a rounded nose 251, and the hub has a thrust receiving face 243 which member 250 is guided to bear against without any torque-transmissive coupling.

Figure 4:
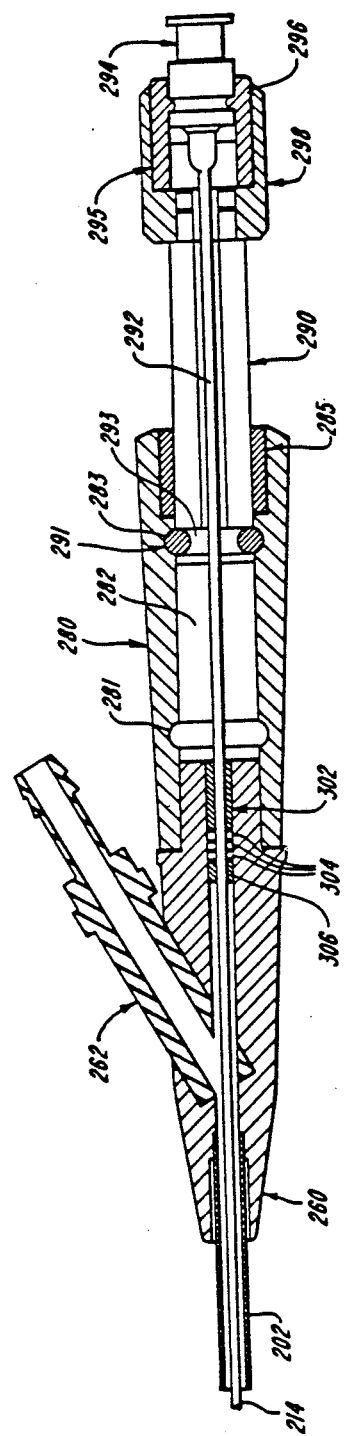
FIG. 4 is a detailed cross-sectional view of the handle portion of the embodiment of FIG. 3.

FIG. 4 is a detailed cross-section of the handle portion 200 of the embodiment of FIGS. 3–3C. Handle 200 has a front portion constituting a bifurcated manifold 260 with an inflation port fitting 262 of conventional type communicating with the inflation tube 202, and an axial passage extending therethrough for holding the inner tube 214. A rear portion 280 constitutes an actuator housing having a central bore 282 axially aligned with the manifold 260 and cooperating with an axially movable member 290 to move a blunt needle/tube assembly 292 back and forth. Tube 292 is attached at one end to a needle connector 294 which is fastened to member 290 by a means of a bushing 295, roller pin 296 and knurled knob 298. Bushing 295 is cemented into knob 298, which in turn, retains the pin 296 in its hole to provide a rigid assembly.

The tube 292 extends through a first bushing 302, O-ring seals 304 and a second bushing 306 into the bifurcated manifold 260, where it is bonded to inner tube 214 (FIG. 3) to provide a fluid-tight coupling therewith. Needle connector 294 and tube 292 thus provide an access port for the inner, fluid-sampling tube 214.

The axially movable member 290 is cross-drilled at its tip, and a pair of small ball bearings 291 are held in the holes under tension by springs 293 to serve as detents. The spring loaded balls snap into grooves 281, 283, located at the advanced and retracted positions, respectively of the actuator housing 280. An optional grooved insert 285 may be bonded to the actuator housing 280 to engage a longitudinal guide rib or ridge formed on member 290 to prevent rotation of the assembly as it is moved.

The actuator thus serves to advance the inner tube 214 when the knurled knob 298 is advanced. In use, the extending member 250 described with reference to FIGS. 3B and illustrated in FIG. 5, below, is inserted fully into tube 292 to engage the tip assembly of the balloon, and is locked in position by a Luer fitting at 294. Knob 298 is then pushed forward to advance both the extender member 250 and tube 214, with respect to the outer tube 202. Since the outer and inner tubes are connected to the proximal and distal ends of the balloon, their relative motion stretches the balloon by an amount equal to the motion of the knob 298.

FIG. 5 shows the extending member 250, which in one prototype embodiment is approximately one hundred twenty-five centimeters in length. The distal end of this embodiment is formed with the aforesaid engaging finger 253, and the proximal end is affixed with a high friction locking adhesive 309 to a cap 310 and Luer tapered plug 308. A lock nut 312 surrounds plug 308 for engaging the fitting 294 of the handle 200 (FIG. 4) to lock the member 250 in the assembly.

Figure 6B:
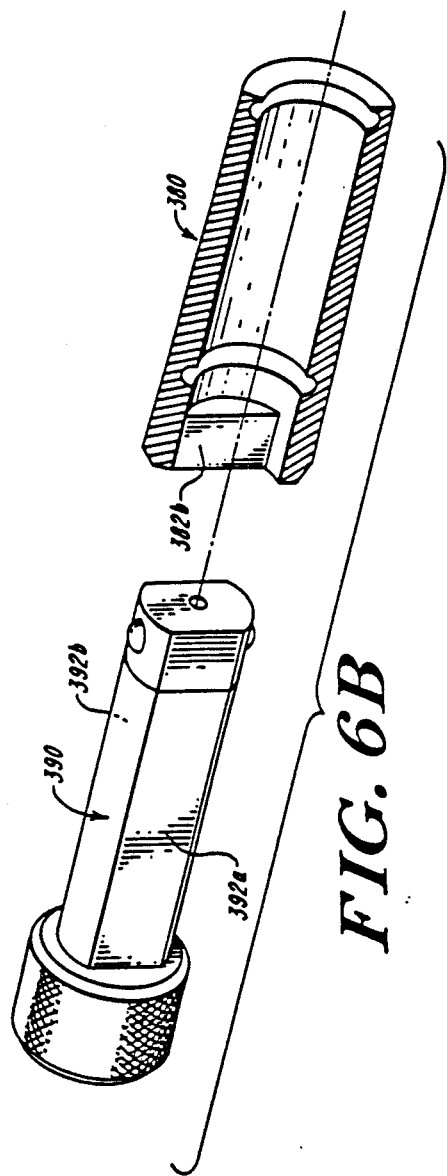

FIGS. 6A, 6B show a sectional and an exploded view of modified details of another embodiment of a stretch wrapping mechanism according to the invention. In this embodiment, the cooperating portions 390, 380 correspond to the portions 290, 280 just described, and the overall construction features are similar. A flat face 392b of the extender handle portion cooperates with a flat guide face 382b in the handle assembly to prevent turning of the inner assembly, i.e., the inner tube and extender member (not shown).

Figure 7B:
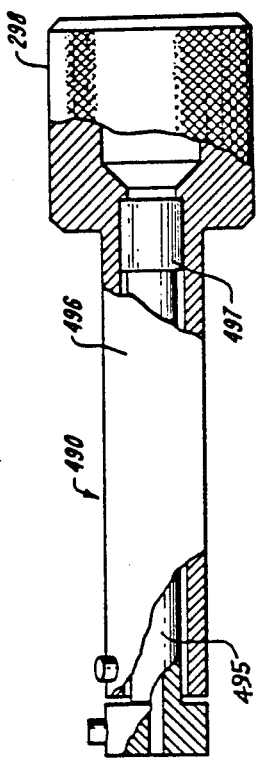
FIGS. 7A, 7B illustrate another embodiment of a balloon extension mechanism.
Figure 7A:
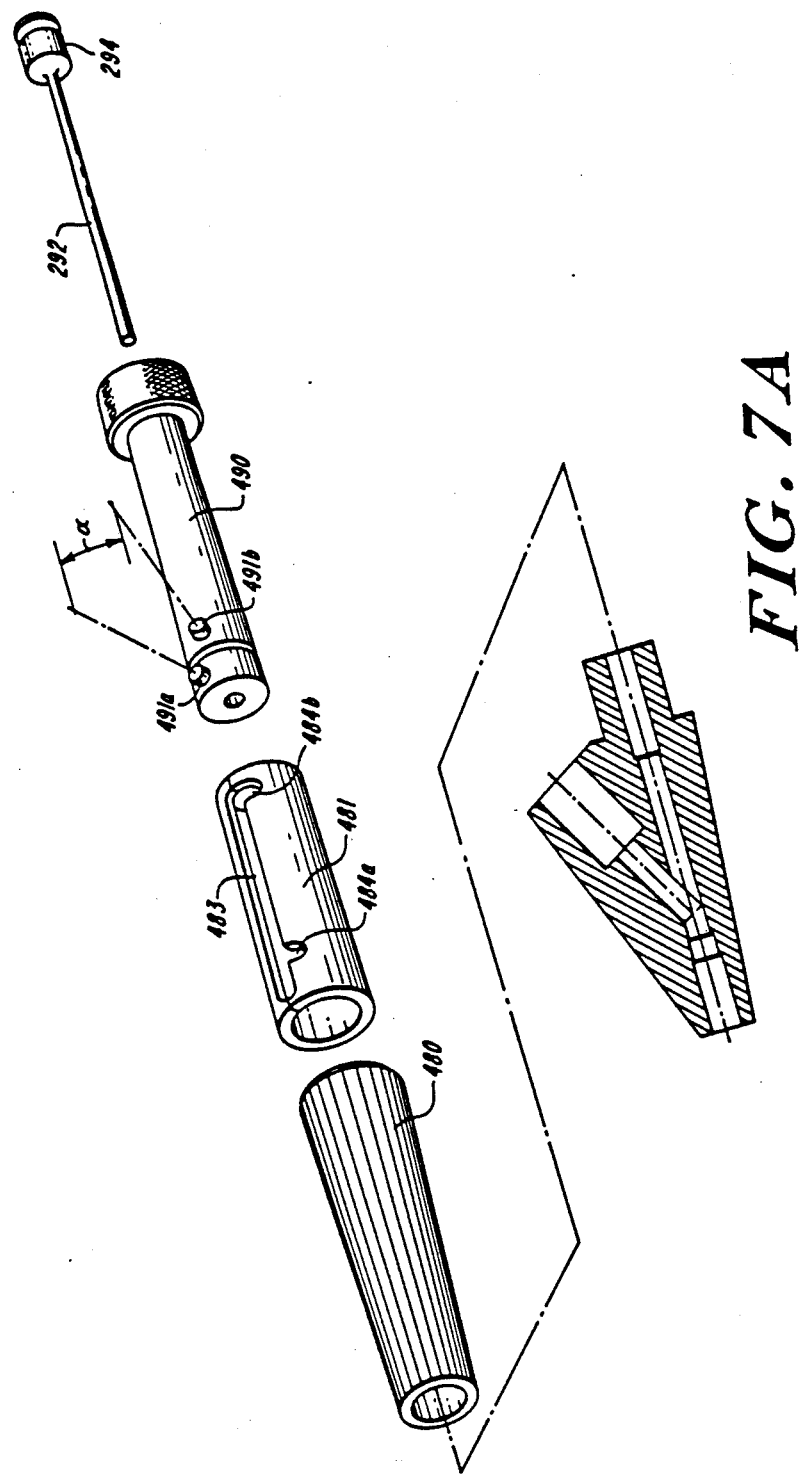

FIG. 7A, 7B illustrate yet another embodiment of a balloon extension mechanism. In this embodiment, a rear portion 480 of the manifold handle receives a grooved split bushing 481 within which a lockable shank 490 moves back and forth. The shank assembly 490 holds a blunt needle assembly identical to the port assembly 292, 294 described with reference to FIG. 4, which is attached to an inner tube 214, as previously described.

The split bushing 481 has an elongate groove 483 with laterally extending notches 484a, 484b, positioned in the manner of a locking drawbolt. The shank assembly 490 has a pair of protruding posts 491a, 491b, each of which has a width narrower than that of groove 483, but which are offset an angle $\alpha$ such that the outer edges of the two posts are separated by a lateral distance greater than the groove width. Thus, as the shank 490 slides back and forth within bushing 481, the split bushing applies a gentle pressure against the posts forcing them into alignment with each other by elastic rotation of post shaft 495 relative to shank 490. Post shaft 495 is formed of a suitable elastic material and is secured to shank 490 at one end. When post 491b is aligned with a notch 484a or 484b, the shank rotates, slipping the post into the notch and thereby stopping the shank at that longitudinal extension. A rotational force must then be exerted on the shank 490 in order to move post 491b out of the notch and permit the shank to move axially. This provides a positive detent or axial stop for the stretch assembly.

FIG. 7B shows a further detail of the construction of the extender shank 490. As shown, an inner post shaft 495 bearing the groove-following post 491a is concentrically carried by, and cemented at its extreme end 497 to the outer shank sleeve 496. The outer shank sleeve 496 carries both the manipulation knob 298 and blunt needle assembly 294, 292, as well as the second, locking, post 491b. The inner sleeve 495 may be formed of an elastic material such as a hard rubber or soft plastic so that when the two posts are urged together by the groove walls the sleeve 495 twists slightly, providing a gentle torsional force which urges posts 491a, 491b apart. This provides the spring loading to snap post 491b into a notch.

The foregoing description illustrates various embodiments of a mechanism which stretches a bladder or balloon in a precise manner at the end of a catheter, while still providing one or more lumens for balloon inflation and fluids monitoring. In the preferred embodiment employing a steel tubular extender member, a relatively soft IABP structure may be stiffened and straightened for insertion along an arterial path over a guide wire.

Such embodiments being thus disclosed, adaptations and modifications thereof will occur to those skilled in the art, and all such variations are within the scope of the invention. Among other variations presently contemplated by the inventors, the relative motions of the outer and inner tubes may be interchanged, so that the handle retracts the outer inflation tube 202. Also, the precise advancing mechanism may be varied. Further, the manifold 260 and actuator section 280 may be designed as separate or separable units, so that the relatively bulky actuator 280 may be removed after the balloon has been inserted in an artery. Other variations will occur to those skilled in the art, and all such modifications and variations are included within the scope of the invention, as set forth in the claims appended hereto.

What is claimed is:

1. A balloon insertion assembly for inserting a balloon along an arterial path to the vicinity of the aorta, such assembly comprising:
   a handle,
   a catheter operatively connected to the handle and extending to a distal catheter end,
   a balloon having a balloon proximal end sealed to the catheter distal end and a balloon distal end separated from said balloon proximal end,
   a thrust-imparting extension member operatively connecting said balloon distal end and a portion of the handle,
   a fluid sampling tube extending within the catheter between said portion of the handle and said balloon distal end, and wherein said thrust-imparting extension member extends within said fluid sampling tube, and
   extension means, in said portion of the handle, for causing a substantially twist-free advancing motion of said extension member with respect to said catheter by simultaneously advancing the fluid sampling tube and the extension member to elongate the balloon and compact it for insertion along an arterial passage.

2. The assembly of claim 1, wherein said extension means includes plural detents defining an advancing motion between (0.15) and (0.75) times the distance between said balloon distal end and said balloon proximal end.

3. The assembly of claim 2, wherein said extension member includes means for irrotationally coupling said extension means end to sad balloon distal end.

4. The assembly of claim 2, wherein said extension member is a hollow member defining a passage effective to follow a guide wire.

5. The assembly of claim 2, wherein said extension means includes a port assembly communicating with a lumen of said fluids sampling tube, and also include a slide mechanism for sliding said port assembly back and forth in said handle.

6. The assembly of claim 5, wherein said extension member is insertable through said port assembly into said fluids sampling tube, and is removably lockable to the port assembly so that motion of the slide mechanism causes equal motion of said extension member, said fluids sampling tube and said balloon distal end.

7. The assembly of claim 6, wherein said balloon includes a proximal end wall, a middle peripheral wall and a distal end wall, said walls together forming a closed envelope, and wherein a said end wall meets said middle peripheral wall at an obtuse angle.

8. The assembly of claim 6, wherein said balloon is non-symmetric.

9. The assembly of claim 6, wherein said balloon has envelope dimensions of approximately twenty-five millimeters diameter by fifty millimeters length.

10. The assembly of claim 7, wherein said slide mechanism includes a locking sleeve.

11. The assembly of claim 10, wherein said slide mechanism includes a shank member supporting said port assembly and having torsionally-biased protrusions extending therefrom and defining locking detents.

* * * * *

UNITED STATES PATENT AND TRADEMARK OFFICE
CERTIFICATE OF CORRECTION

PATENT NO. : 4,968,300

DATED : November 6, 1990

INVENTOR(S) : Moutafis et al.

It is certified that error appears in the above-identified patent and that said Letters Patent is hereby corrected as shown below:

Column 4, line 8, please replace "tube" with --tubing--.

Column 8, line 18, please replace "include" with --includes--.

Signed and Sealed this

Eighteenth Day of August, 1992

Attest:

DOUGLAS B. COMER

*Attesting Officer*     *Acting Commissioner of Patents and Trademarks*